US007288763B2

(12) United States Patent
Ikeda et al.

(10) Patent No.: US 7,288,763 B2
(45) Date of Patent: Oct. 30, 2007

(54) METHOD OF MEASUREMENT ACCURACY IMPROVEMENT BY CONTROL OF PATTERN SHRINKAGE

(75) Inventors: Satoshi Ikeda, Hitachinaka (JP); Hiroki Kawada, Tsuchiura (JP); Atsushi Kobaru, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 15 days.

(21) Appl. No.: 11/405,456

(22) Filed: Apr. 18, 2006

(65) Prior Publication Data

US 2006/0192119 A1   Aug. 31, 2006

Related U.S. Application Data

(63) Continuation of application No. 11/009,393, filed on Dec. 13, 2004, now Pat. No. 7,045,782.

(30) Foreign Application Priority Data

Dec. 15, 2003  (JP) ............................. 2003-417128

(51) Int. Cl.
*H01J 37/28*    (2006.01)
*H01J 37/256*   (2006.01)

(52) U.S. Cl. .................. 250/310; 250/306; 250/491.1; 250/492.2

(58) Field of Classification Search ..................... None
See application file for complete search history.

(56) References Cited

U.S. PATENT DOCUMENTS

| 5,276,325 | A | 1/1994 | Todokoro et al. |
| 6,867,606 | B2* | 3/2005 | Pinto et al. ................. 324/751 |
| 7,045,782 | B2* | 5/2006 | Ikeda et al. ................. 250/310 |
| 2005/0006598 | A1 | 1/2005 | Pearl |

FOREIGN PATENT DOCUMENTS

JP    2001-147112    5/2001

OTHER PUBLICATIONS

L. Reimer, "Scanning Electron Microscopy", Springer-Verlag Berlin and Heidelberg GbmH & Co., KG, 1985, p. 12-57.

* cited by examiner

*Primary Examiner*—Nikita Wells
(74) *Attorney, Agent, or Firm*—McDermott Will & Emery LLP (57) ABSTRACT

A scanning method for a scanning electron microscope is provided which minimizes a degradation in dimension measuring accuracy caused by a shrink of a specimen. A time between the first and the second scan over the same location on the specimen is shortened by changing the scanning order of scan lines to enable the scanning to be performed successively while the shrink is small.

5 Claims, 9 Drawing Sheets

CONTINUOUS SCANNING (WHEN 8 FRAMES ARE COMBINED)

INTERLACED SCANNING
SCANNING ORDER   MONITOR SCREEN

METHOD OF MEASUREMENT ACCURACY IMPROVEMENT BY CONTROL OF PATTERN SHRINKAGE

RELATED APPLICATIONS

This application is a continuation of Application 11/009,393, filed Dec. 13, 2004 now U.S. Pat. No. 7,045,782, which claims priority of Japanese Application No. 2003-417128, filed Dec. 15, 2003, the contents of which are hereby incorporated by reference.

BACKGROUND OF THE INVENTION

The present invention relates to a scanning electron microscope to observe a fine pattern to measure its dimensions and more particularly a scanning electron microscope designed to take measurements of samples whose shape changes as they are applied with an electron beam.

In a manufacturing and inspection process of functional element products, such as semiconductor devices and thin-film magnetic heads, which are fabricated by a surface microfabrication technique, a scanning electron microscope is widely used for measurement of widths of patterns fabricated (referred to as "critical dimension measurements") and for external inspection. The scanning electron microscope forms an image of a sample in a sequence of steps that involves: linearly or two-dimensionally scanning an electron beam, which is emitted from an electron source and finely focused by a converging lens or objective lens using interactions between a magnetic field or electric field and the electron beam, over the sample using a beam deflector; detecting a secondary signal (secondary electrons and back-scattered electrons) produced by the electron beam by using a photoelectric effect-based detector; and transforming the detected signal into a visible signal, such as a luminance signal synchronous with the scanning of the electron beam.

In scanning electron microscopes, provisions are made to ensure that an image of a specimen obtained depicts, with high precision, features of a specimen surface being observed and measured. That is, when the specimen surface is examined, visualization points of the image signal are arranged at positions precisely similar to those positions of the corresponding points in an area being scanned. To realize this position matching, the scan area and the image area are both set rectangular in shape and made up of the same number of scan lines whose length is equal to one side of the rectangle. Generally, the scan area and the image area are set to have the same ratio of a scan line length to a distance between the adjoining scan lines. With this arrangement, a distance between any two points on the specimen surface has a constant ratio to a distance between the corresponding two points in the image of the specimen at all times. This ratio signifies a magnification of the scanning electron microscope. Such a technology has been widely implemented as a basic technology in the scanning electron microscopes, as described in L. Reimer, "Scanning Electron Microscopy", Springer-Verlag Berlin and Heidelberg GmbH & Co. KG, 1985, page 2, for example. From the specimen image thus obtained, the distance between any two points on the specimen surface can be calculated easily. This calculation is generally called "critical dimension measurement" and a scanning electron microscope with such a calculation function is called a "critical dimension scanning electron microscope."

An example case where the scan area on the surface of a specimen and the corresponding specimen image are not similar is described in JP-A-2001-147112. In this example, for a specimen with patterns so spaced apart as to make it necessary to measure dimensions with a reduced magnification although the patterns are very fine, a secondary electron image is formed by extending the specimen image in a direction perpendicular to a line connecting two points on the specimen, thereby improving the measurement accuracy.

Such a scanning electron microscope therefore needs to radiate against the surface of the specimen being probed an electron beam with a surface arrival energy of several hundred electron bolts.

As features of microfabricated semiconductor surfaces have become more and more miniaturized in recent years, a photoresist that reacts to an argon fluoride (ArF) excimer laser beam (referred to as an "ArF resist") has come to be used as a photosensitive material for photolithography. The ArF laser beam has a short wavelength of 193 nm and thus the ArF resist is considered suited for exposing finer circuit patterns. Our recent study, however, has found that the ArF resist is very fragile when subjected to electron beams and that, when a fabricated pattern is probed or its critical dimensions are measured by a scanning electron microscope, a base material such as acrylic resin is condensed by the focused electron beam, reducing its volume (referred to as a "shrink") and deforming the circuit pattern.

To realize a design performance of semiconductor devices requires a stringent control of shapes and dimensions of circuit patterns and, for this reason, a critical dimension scanning electron microscope capable of measuring very fine dimensions is used in an inspection process. However, if the shape of a pattern changes upon application of a critical dimension measuring electron beam during the observation and measurement processes, an expected design value of the circuit pattern dimension cannot be realized, leading to a problem of degradation of device characteristics and failures. Further, since line widths change when subjected to an electron beam, a measured value of the same dimension may vary each time a measurement is made, making it impossible to improve the measurement accuracy. At present, no other equipment than the critical dimension scanning electron microscope is available that can measure fine dimensions at a satisfactory precision. So, the pattern shrink poses a serious problem to the semiconductor device manufacture using an ArF resist. Conventional scanning electron microscopes, as described above, do not provide a means to deal with the shrink of a specimen caused by the electron beam and there is a problem with measured values of pattern dimensions. Further, in the case of the JP-A-2001-147112 described above, although the measurement accuracy of a dimension between two separate points on a specimen is taken into consideration, no provisions are made to deal with the shrink of specimen caused by the application of an electron beam.

It is an object of this invention to provide a scanning electron microscope capable of measuring a pattern formed on a specimen that shrinks upon being radiated with an electron beam, such as an ArF resist.

The shrink of an ArF resist pattern is considered to be a chemical reaction caused by the energy of a focused electron beam incident on the resist. It is thus considered that the volume of the ArF resist will change after the irradiation of electron beam according to an equation (1) below.

$$V_s = V \exp(-t/\tau) \quad (1)$$

where Vs is a volume of the ArF resist after being irradiated with an electron beam, V is a volume of the ArF resist before the application of the electron beam, τ is a time constant of the chemical reaction in the ArF resist, and t is an elapsed time.

As can be seen from equation (1), there is a time lag from when an electron beam is radiated against the ArF resist until the resist shrinks by a reaction. When a scanning electron microscope is used to make measurements, since an image formed in only one scan (1 frame) has a poor S/N ratio, it is common practice to overlap a plurality of frames and produce an averaged image to improve the S/N ratio and thereby enhance the measurement accuracy. Based on the fact that (1) there is a time lag from an instant the ArF resist is irradiated with an electron beam until a reaction takes place and that (2) normally a plurality of frames are overlapped to form a target image for dimension measurement, we have studied measures to deal with the problems described above.

Figure 1A:
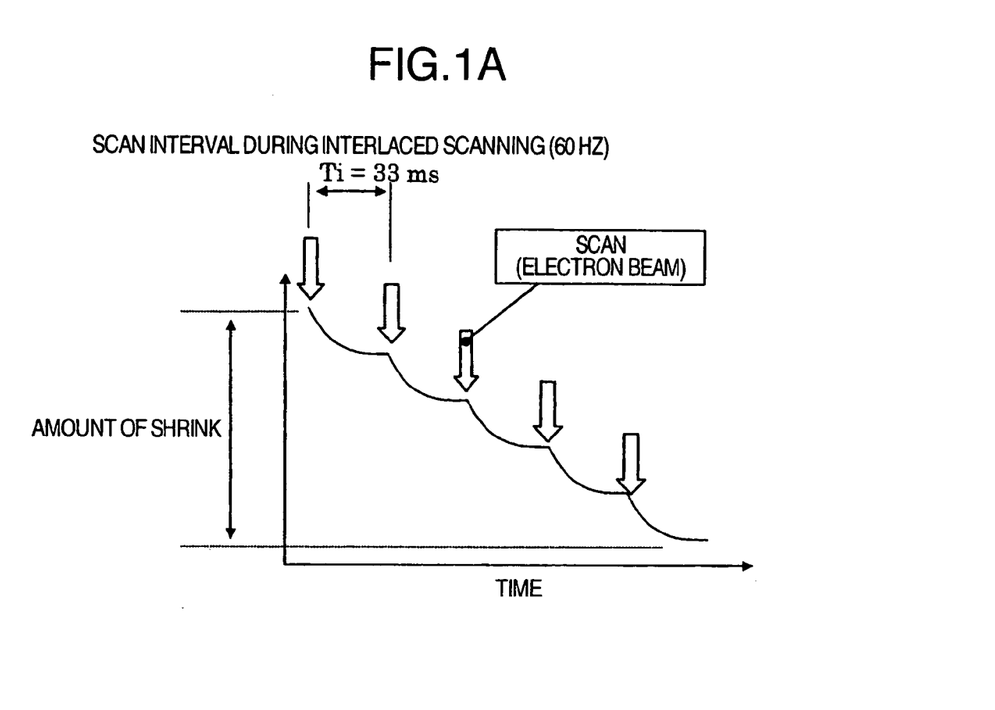
FIGS. 1A-1B are diagrams showing a relation between scanning methods and the amount of shrink.
Figure 1B:
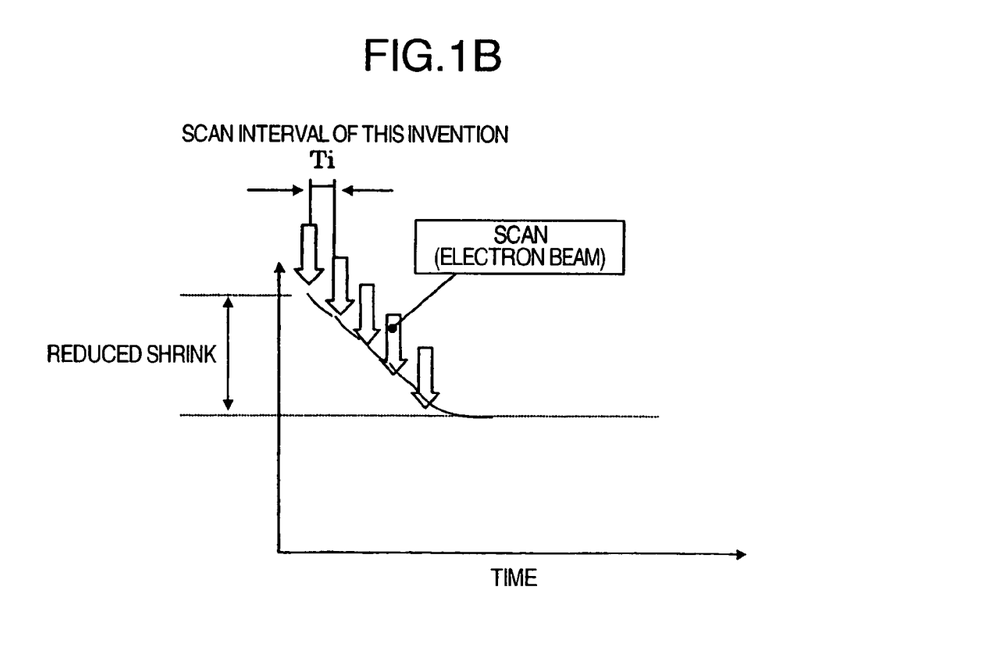

Suppose a time which elapses from when an electron beam scan is performed once over a specimen until the next scanning electron beam reaches the same position on the specimen is Ti and that a time constant of the chemical reaction of the ArF resist is τ according to equation (1). In an interlaced scan at 60 Hz, Ti was 33 ms and, in an experiment performed by the inventor, τ was 5 ms. At this time, Ti>τ and the second electron beam scan is executed after the shrink of the ArF resist has progressed significantly (see FIG. 1A). On the contrary, this invention has Ti<<τ (see FIG. 1B). By shortening the scan interval, it is possible to make precise measurements with a reduced amount of shrink.

That is, a highly accurate measurement is made of a resist such as an ArF resist that shrinks when subjected to an electron beam, by changing a scanning order of scan lines to shorten the time between the first and the second scan over the same location on the specimen to allow the scans to be performed successively while the amount of shrink is small. The time between the scans can also be shortened by reducing the number of scan lines or shortening the scan width. Further, a user is provided with an environment that makes for an easier use of the microscope by registering parameters, such as scanning order, the number of scan lines, scan width and the total number of frames, as fixed values in advance so that the user can choose a desired combination of these at time of taking measurements.

SUMMARY OF THE INVENTION

According to one aspect, the present invention provides a scanning electron microscope comprising: an electron beam source; an electron beam scanning unit to focus an electron beam emitted from the electron beam source and sweep it over a specimen; a detector to detect secondary signals coming out from the specimen when it is subjected to the electron beam; and an imaging unit to form a specimen image by summing up a plurality of image signals based on the secondary signals detected by the detector; wherein a plurality of electron beam scanning patterns are selectably provided in which the electron beam is scanned over the specimen by the electron beam scanning unit; wherein the plurality of scanning patterns have different time periods which elapse after each electron beam radiation position in a scan area on the specimen has received the electron beam until it receives the beam again. A typical scanning pattern is to repeat as many scans over one scan line as the total frame number before moving to the next scan line. The imaging unit may form a specimen image by summing up a plurality of frames of image signals.

This invention permits highly precise dimension measurements for specimens, such as photoresists for an argon fluoride (ArF) excimer laser beam, that are deformed by an electron beam. Further, since this invention does not change the scanning speed of the beam, no significant modification in the equipment structure is needed and therefore this invention can be implemented by only software modification and easily introduced to conventional equipment.

Other objects, features and advantages of the invention will become apparent from the following description of the embodiments of the invention taken in conjunction with the accompanying drawings.

DETAILED DESCRIPTION OF THE EMBODIMENTS

Figure 2:
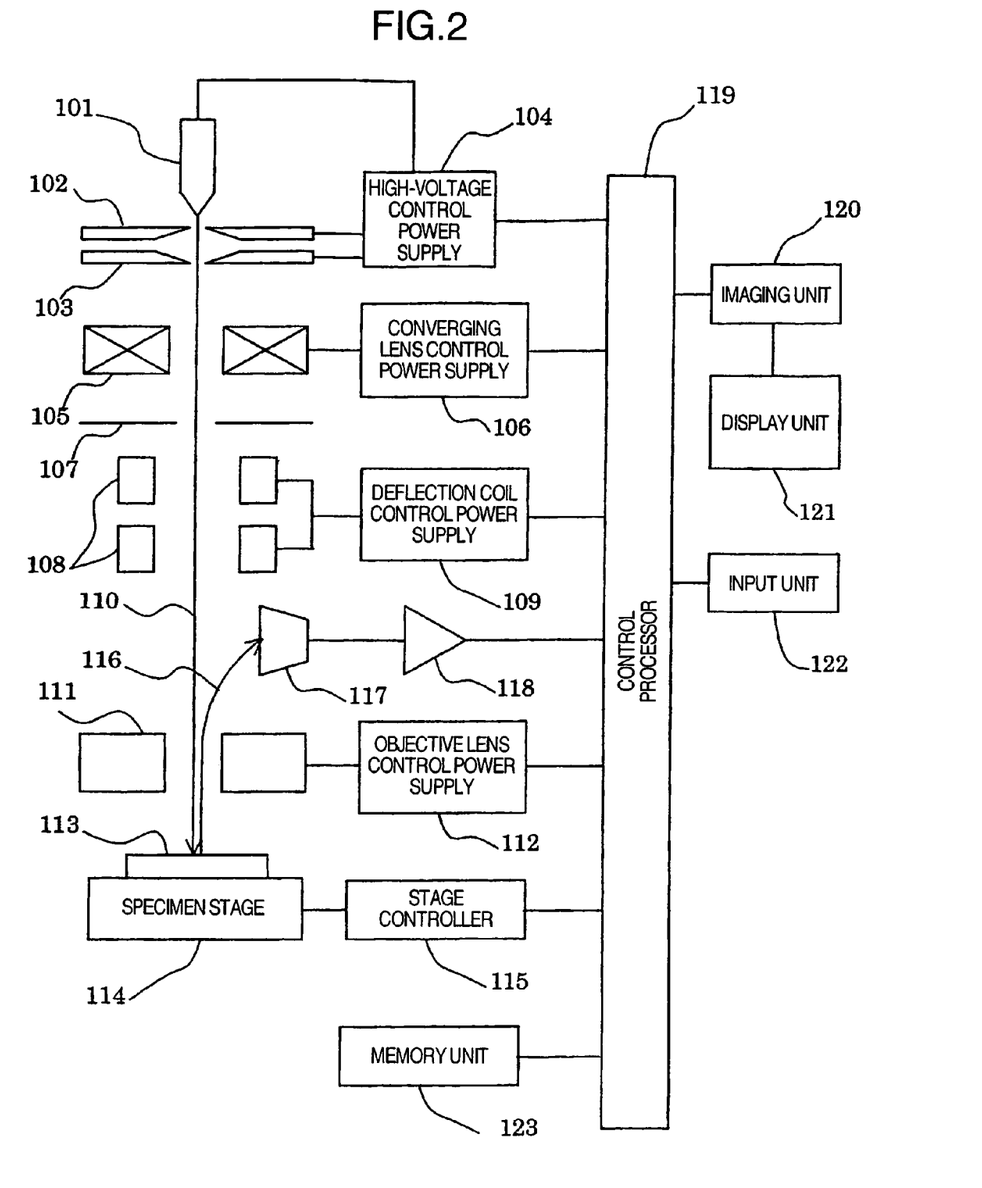
FIG. 2 is a schematic diagram showing one example configuration of a scanning electron microscope according to this invention.

FIG. 2 is a schematic view showing an example construction of a scanning electron microscope according to this invention. An acceleration voltage from a high voltage control power supply 104 controlled by a control processor 119 is applied between a cathode 101 and a first anode 102 to draw a predetermined emission current from the cathode 101. Between the cathode 101 and a second anode 103 is impressed the acceleration voltage from the high voltage control power supply 104 controlled by the control processor 119, so a primary electron beam 110 emitted from the cathode 101 is focused by a converging lens 105 controlled by a converging lens control power supply 106 and then removed of an unwanted peripheral portion by a throttle plate 107.

Then, the primary electron beam 110 is focused into a fine spot by an objective lens 111 controlled by a objective lens control power supply 112. The beam spot is swept two-dimensionally over a specimen 113 by a deflection coil 108. A scan signal for the deflection coil 108 is controlled by a deflection coil control power supply 109 according to a magnification. The specimen 113 is securely placed on a specimen stage 114 that can be moved two-dimensionally. The movement of the specimen stage 114 is controlled by a stage controller 115.

Secondary electrons 116 emitted from the specimen 113 when struck by the primary electron beam 110 are detected by a secondary electron detector 117 and amplified by a secondary electron signal amplifier. An imaging unit 120 transforms the detected secondary signals into visible signals that are arranged on a separate plane and shows on a display unit 121 an image that precisely represents a surface topography of the specimen. An input unit 122 provides an interface between an operator and the control processor 119. Using the input unit 122, the operator controls various units, specifies points to be measured and issues a command for dimension measurement.

While in FIG. 2 the control processor has been described to be integrated in the scanning electron microscope or configured in a similar manner, other configurations may also be employed. For example, the control processor may be arranged as a separate unit from the scanning electron microscope and assigned with processing described in the following. In that case, additional components are required, which include: a transfer medium that transfers signals detected by the secondary electron detector 117 to the control processor or transfers signals from the control processor to the lenses and deflection coil in the scanning electron microscope; and input/output terminals that input and output signals via the transfer medium. It is also possible to register with a memory unit 123 a program for performing the processing described below and have the program executed by the control processor 119 that has an image memory and supplies necessary signals to the scanning electron microscope.

Measurement of a pattern dimension involves, for example, having two vertical or horizontal cursor lines displayed on the display unit 121 together with a specimen image and aligning the two cursors with pattern edges by operating the input unit 122. Based on information about a distance between the two cursors, the control processor 119 calculates a measured value as a dimension of the pattern.

Stored in the memory unit 123 is information on a scanning pattern which includes a plurality of control data for determining the order of scan, a plurality of control data for determining the number of scan lines, a plurality of control data for determining a scan width, and a plurality of values representing the total numbers of frames. When starting the measurement, an operator selects and specifies, from among scan methods displayed on a scan method selection page, a desired condition suited for a specimen to be measured including the scan order, scan line number, scan width and total frame number. With a desired scan method determined, the control processor 119 retrieves control data corresponding to the selected condition from the memory unit 123 and, by using the control data retrieved, controls the deflection coil control power supply 109 to sweep the electron beam in a desired scanning pattern over the specimen. Initiating the measurement as described above allows an image to be retrieved according to the scanning method modified by the user and therefore a precise measurement to be made based on the retrieved image.

Figure 3:
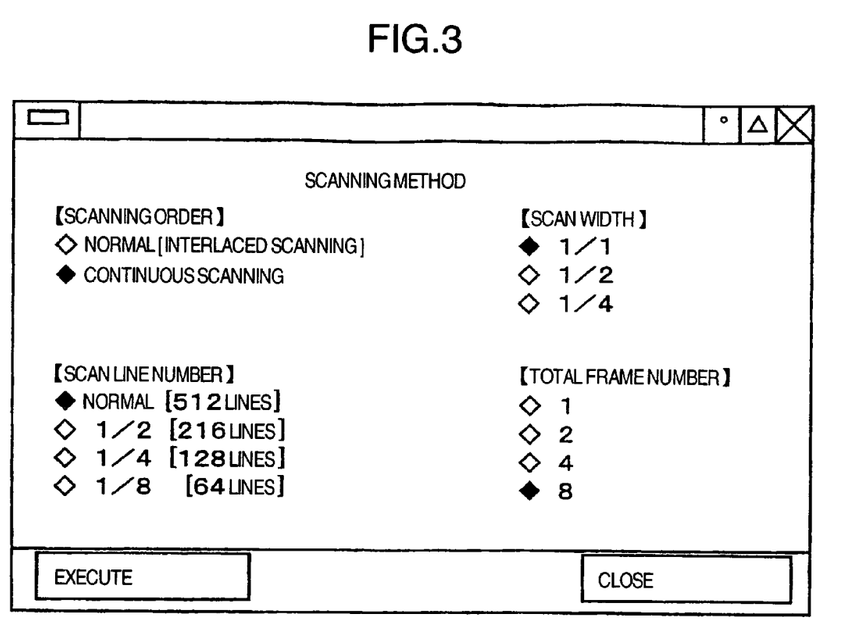
FIG. 3 shows an example of a scanning method selection page.

FIG. 3 shows an example scanning method selection page. On this scanning method selection page the user can selectively specify a desired electron beam scanning method used in creating an image of the sample. Shown on this scanning method selection page as selection items are scanning order, scan line number, scan width and total frame number. FIG. 3 shows that a continuous scanning is chosen as the scan order, normal 512 lines as the number of scan lines, ⅟₁ as the scan width, and 8 as the total number of frames.

First, the "scan order" will be explained. "Normal (interlaced scanning)" shown as one choice of scanning order is an interlaced scanning normally used in conventional scanning electron microscopes, and "continuous scanning" is the one used in this invention. A difference in the scanning order between the conventional normal scanning (interlaced scanning) and the continuous scanning of this invention will be explained by referring to FIG. 4 and FIG. 5.

Figure 4A:
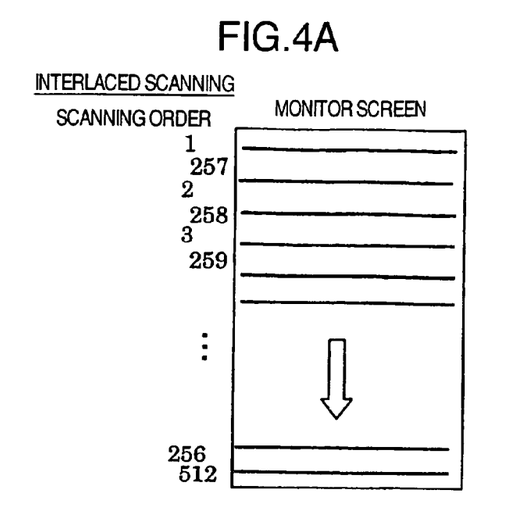
FIGS. 4A-4C show how a normal scanning (interlaced scanning) is performed.

FIG. 4 explains the order of scanning during the normal scanning (interlaced scanning). As shown in a monitor screen diagram of FIG. 4A, the normal scanning is the same interlaced scanning as used in TV. Let us take an example case of 512 scan lines. In this example, a first scan is made in the horizontal direction from upper left corner of the screen to upper right corner. The similar scanning operation is repeated by moving the starting point of scan vertically down until 256th scan is executed. Then, the scan starting point is moved up to a position between the first scan line and the second scan line where a 257th scan is executed. This is followed by a 258th scan performed between the second scan line and the third scan line. Such a scan is repeated until 512th scan is completed, thus forming one frame of image. While the order of scan has been explained on the monitor screen, the specimen is also scanned by an electron beam in the same order as described above. With this scanning method, in the case of 60-Hz TV scan one frame takes 33 ms. For example, when eight frames of image signal are combined to form an image, this interfaced scanning is repeated eight times.

Figure 4B:
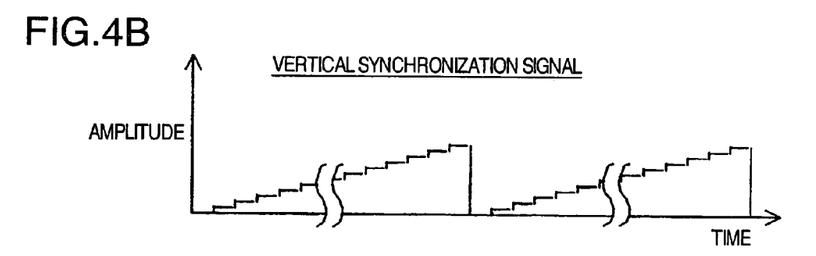
Figure 4C:
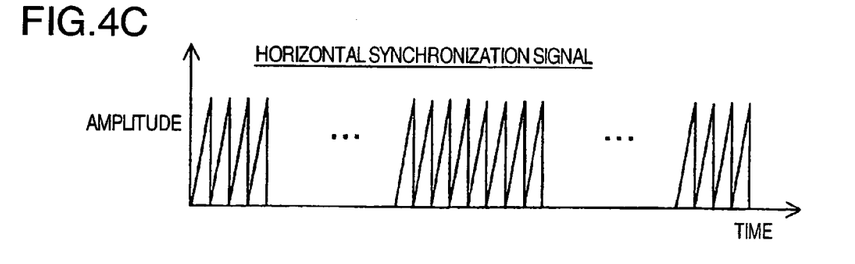

FIG. 4B and FIG. 4C schematically show a vertical synchronization signal and a horizontal synchronization signal for the normal scanning (interlaced scanning). Both the vertical synchronization signal and the horizontal synchronization signal are basically of sawtooth waveform. While the vertical synchronization signal describes one sawtooth wave, the horizontal synchronization signal describes 256 sawtooth waves. This is repeated two times to form one frame of image.

However, in the case of a specimen which may sustain physical or chemical changes when subjected to an electron beam during a plurality of scans of the above scanning method, such as an ArF resist that shrinks upon beam application, pattern dimensions may change due to irradiation of the electron beam, making a precise, stable measurement of dimensions impossible. A conventional practice to reduce a shrink of resist due to application of an electron beam requires reducing the amount of electron beam emitted or lowering the measuring magnification, which in turn gives rise to other problems of a degraded S/N ratio of secondary electron signal and lowered measuring and reproduction precisions caused by a reduced magnification. One of scanning methods that can avoid these problems is the continuous scanning adopted by this invention.

Figure 5A:
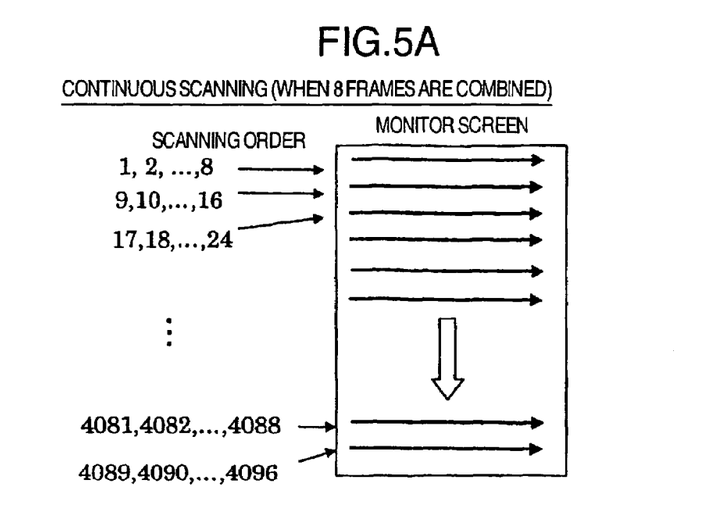
FIGS. 5A-5C show how a continuous scanning is performed.
Figure 5B:
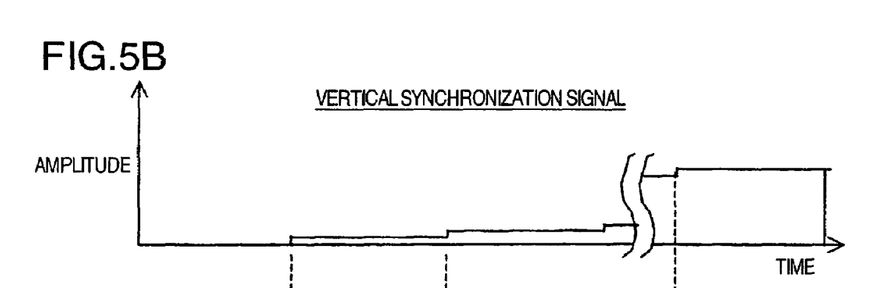
Figure 5C:
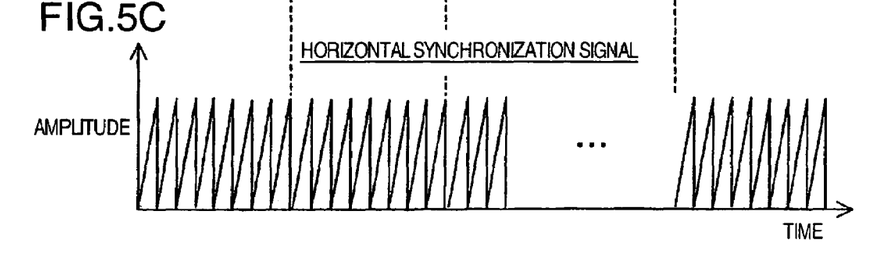

Referring to FIG. 5, the continuous scanning of this invention will be described. FIG. 5A shows the order of scan lines on the monitor screen for the continuous scanning. FIG. 5B and FIG. 5C show a vertical synchronization signal and a horizontal synchronization signal, both used to realize the continuous scanning. Here, an example case is taken up where one frame is made up of 512 scan lines and eight such frames of image signal are combined to produce a measured image.

In the continuous scanning, the deflection coil control power supply 109 controls a scan signal for the deflection coil 108 to sweep the beam along as many scan lines as used in the conventional method, 512 scan lines per frame, in an order shown in FIG. 5A, which differs from the conventional order of scanning and in which the scanning is performed along each scan line as many times continuously as the number of frames to be combined. That is, on the monitor screen, the uppermost scan line is first scanned for eight frames continuously. Next, the scanning start point is moved to the second scan line which is then scanned for eight frames continuously. In this way each scan line is scanned as many times successively as the number of frames to be combined. In the final step, the bottom scan line is scanned for eight frames continuously. The image of the sample is formed by combining the eight frames of pixel signals for each scan line. While the order of scanning has been explained by referring to the monitor screen, the electron beam is also scanned over the sample in the order described above. When the total number of frames per image is changed, the number of times that each of the scan lines is scanned successively also changes. When, for example, the total frame number is changed to four, each of the 512 scan lines is scanned four times in succession before moving to the next scan line, and the resulting image signals are used to form an image of the specimen.

Compared with the conventional method, this continuous scanning has the same magnification but the time it takes for the beam to reach the same location on the specimen a second time after the first time is reduced to one 512th. If a 60-Hz scanning is considered, the time Ti which elapses from the instant a certain point on the specimen is scanned (by an electron beam) until it is scanned again is 33 ms in the conventional normal interlaced scanning method, whereas the continuous scanning reduces the time Ti to about 0.064 ms, which is sufficiently smaller than the chemical reaction time constant for ArF resist, $\tau=5$ ms, to realize a target condition of Ti<$\tau$. Therefore, in the scanning process that overlaps a plurality of frames to produce an image of the specimen, since the scanning to retrieve image signals is done while the shrink is small, the measurement accuracy can be made higher than when measurements are made by using a specimen image formed by the conventional interlaced scanning of an electron beam.

The horizontal synchronization signal for the continuous scanning is similar to the one used in the conventional interlaced scanning, as shown in FIG. 5C. However, the vertical synchronization signal differs from that of the interlaced scanning and has a steplike waveform, as shown in FIG. 5B. In one step of the vertical synchronization signal, as many horizontal synchronization signals as the total frame number (e.g., eight horizontal synchronization signals when the total frame number is eight) are produced.

Returning to the scanning method selection page of FIG. 3, a procedure for setting the number of scan lines will be explained. In the example of FIG. 3, the number of scan lines making up one page of image can be chosen from among normal (512 lines), ½ (216 lines), ¼ (128 lines) and ⅛ (64 lines). By controlling the scan signal for the deflection coil 108 by the deflection coil control power supply 109, the number of scan lines making up one page of image can be reduced to shorten the time it takes to retrieve one frame of image signals. That is, the time interval can be shortened which elapses from the moment an image signal is retrieved for a certain frame until an electron beam is radiated against the same location on the specimen to retrieve an image signal for the next frame. This method for reducing the number of scan lines is effective when measuring line widths of, for example, a line pattern.

Figure 6A:
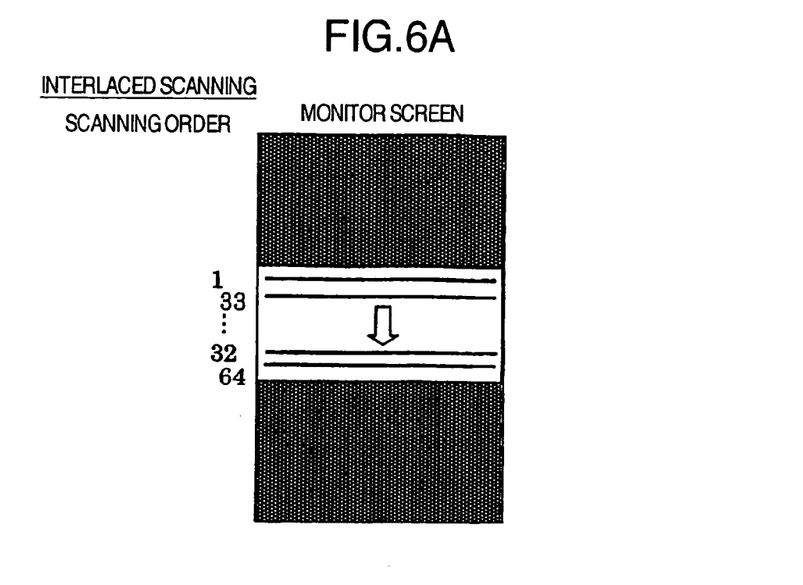
FIGS. 6A-6C show how a scanning is performed when the number of scan lines is changed.

FIG. 6 shows an order in which the scan lines are scanned when 64 lines, one eighth of the normal number, are chosen as the number of scan lines. Here, our explanation assumes that the normal (interlaced scanning) is selected as the order of scanning and ⅟₁ as the scan width. FIG. 6A shows a range of image displayed on the monitor screen and an order of scanning. The monitor screen is so set that the specimen image is displayed on the entire screen when the number of scan lines is 512. If the number of scan lines is set to 64, one eighth of 512, a vertical dimension of the displayed image is one eighth of that of the monitor screen. Although the scanning order and the scanning range have been explained on the monitor screen, the electron beam is also swept over the specimen in a scan range that is narrowed in the sub-scan direction. Changing the number of scan lines naturally changes the width of the scan area in the sub-scan direction. For example, when the number of scan lines is set to ½, the vertical dimension of the image displayed on the monitor screen is ½ of the monitor screen size.

Figure 6B:
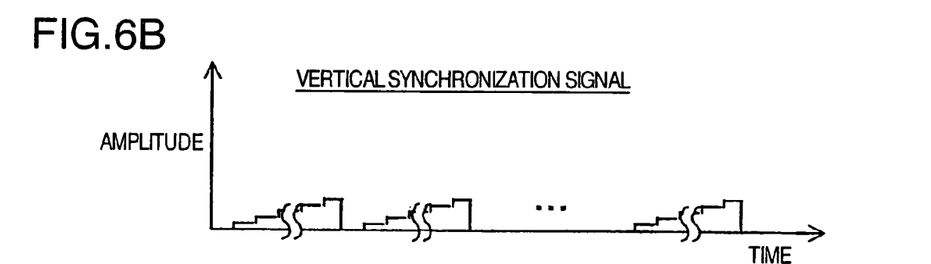
Figure 6C:
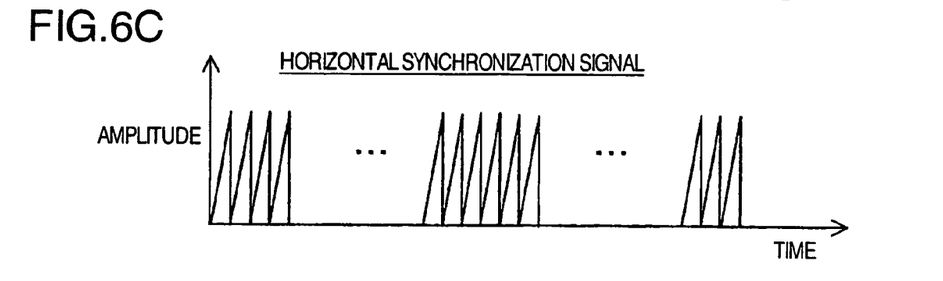

FIG. 6B and FIG. 6C schematically show a vertical synchronization signal and a horizontal synchronization signal, respectively, during the scanning operation. Since the number of scan lines is set to 64 lines, one eighth of the normal 512 lines, the amplitude of the vertical synchronization is one eighth of that when the normal 512 lines are used. The amplitude of the horizontal synchronization signal is the same as that used in the conventional scanning method. By setting the amplitude of the vertical synchronization signal smaller than normal, the period of the vertical synchronization signal is shortened, which in turn reduces the time required to retrieve one frame.

Returning again to the scanning method selection page of FIG. 3, a selection of the scan width will be explained. In the example of FIG. 3, the scan width can be chosen from among ⅟₁ (normal), ½ and ¼. The scan signal for the deflection coil 108 can be controlled by the deflection coil control power supply 109 to change the scan width to reduce a period of the horizontal synchronization signal. This in turn shortens the time required to retrieve one frame of image signals and therefore the time interval which elapses from the moment an image signal is retrieved for a certain frame until an electron beam is radiated against the same location on the specimen to retrieve an image signal for the next frame.

Figure 7A:
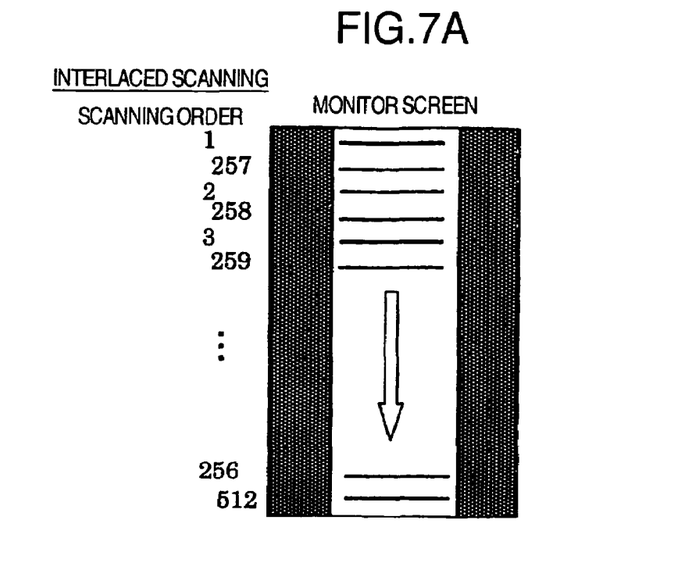
FIGS. 7A-7C show how a scanning is performed when a scan width is changed.

FIG. 7 schematically shows how the scan lines are scanned when ½ the normal scan width is selected. As for other selection items, the normal (interlaced scanning) is chosen as the order of scanning and the normal 512 scan lines are chosen as the number of scan lines. FIG. 7A shows a range of image displayed on the monitor screen and an order of scanning. The monitor screen is so set that the specimen image is displayed on the entire screen when the scan width is ⅟₁ (normal). When the scan width is set to ½, the horizontal width of the image displayed is one-half the width of the monitor screen. While the scanning order and the scanning range have been explained on the monitor screen, the electron beam is also swept over the specimen in a scan range that is reduced in the main scan direction.

Figure 7B:
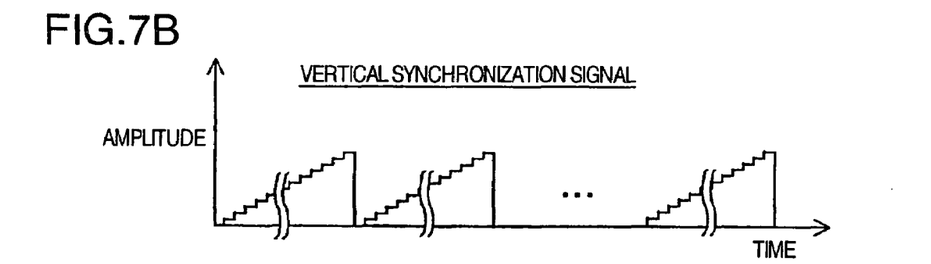
Figure 7C:
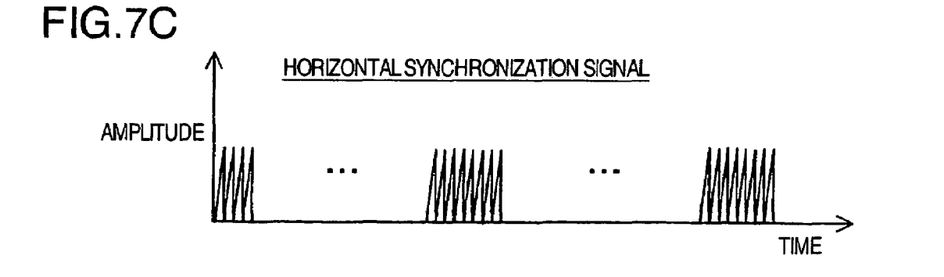

FIG. 7B and FIG. 7C schematically show a vertical synchronization signal and a horizontal synchronization signal, respectively, during the scanning operation. Because the scan width is set to ½ the normal scan width, an amplitude of the horizontal synchronization signal is one-half that when the normal (⅟₁) scan width is chosen. In addition, a period of the horizontal synchronization signal is also one-half the normal. As for the vertical synchronization signal, while its amplitude is the same as that of the conventional scanning method, its period is one-half that of the normal scanning because the period of the horizontal synchronization signal is one-half that of the normal scanning. By setting the scan width smaller than that of the normal scanning as described above, the periods of the vertical and horizontal synchronization signals can be made shorter, reducing the time required to retrieve one frame.

Figure 8A:
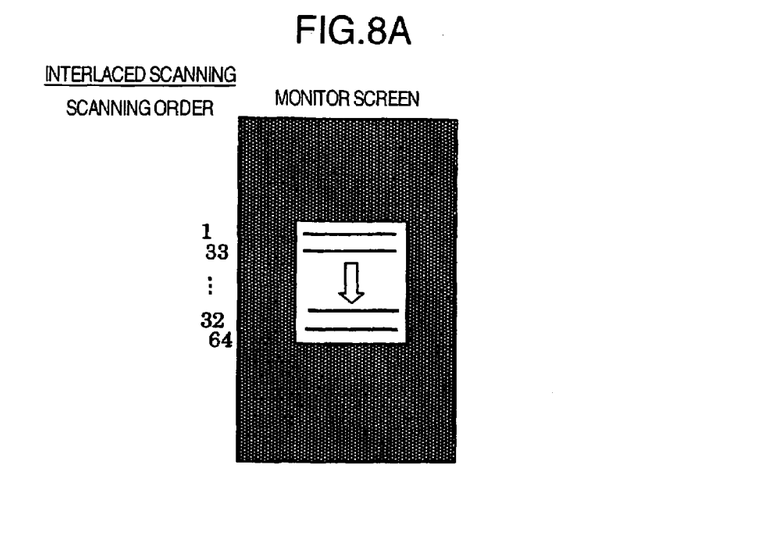
FIGS. 8A-8C show how a scanning is performed when both the scan line number and the scan width are changed.
Figure 8B:
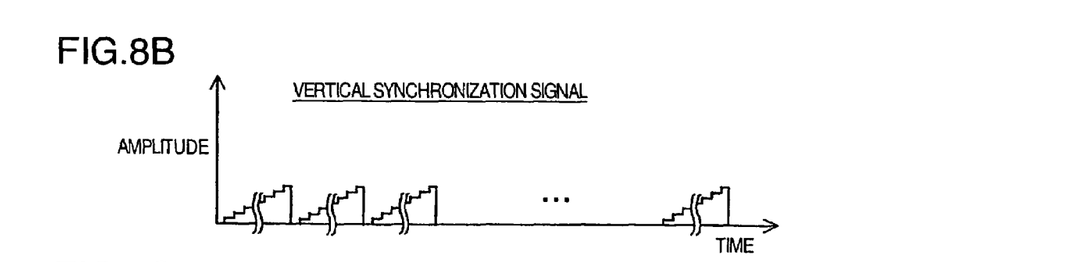
Figure 8C:
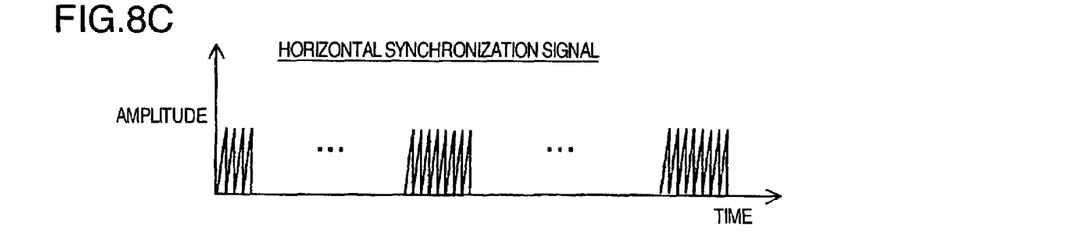

Further, combining the above-described scan line number reducing method and scan width reducing method can enhance the effect of shortening the time required to retrieve one frame. FIG. 8 schematically shows how the scan lines are scanned when the number of scan lines and the scan width are both set smaller than the normal in the selection page of FIG. 3. Here, the normal (interlaced scanning) is chosen as the scanning order, ⅛ (64 lines) as the number of scan lines, and ½ as the scan width.

FIG. 8A shows a range of image displayed on a monitor screen and an order of scanning. The monitor screen is so set that the specimen image is displayed on the entire screen when the number of scan lines is normal (512 lines) and the scan width is ¹⁄₁ (normal). If the number of scan lines is set to ⅛ the normal and the scan width to ½, the vertical dimension of the image displayed is ⅛ the dimension of the monitor screen and the horizontal width is one-half the width of the monitor screen. Although the scanning order and the scanning range have been explained by referring to the monitor screen, the electron beam is also swept over the specimen in a scan range that is narrowed in the main and sub-scan directions.

FIG. 8B and FIG. 8C schematically show a vertical synchronization signal and a horizontal synchronization signal, respectively, during the scanning operation. As for the horizontal synchronization signal, since the scan width is set to ½ the normal scan width, its amplitude is one-half that when the normal (¹⁄₁) scan width is chosen. In addition, a period of the horizontal synchronization signal is also one-half the normal. As for the vertical synchronization signal, since the number of scan lines is set to ⅛, its amplitude is ⅛ of that when the normal number of scan lines (512 lines) is chosen. Further, because the amplitude of the vertical synchronization signal is ⅛ and the period of the horizontal synchronization signal is one-half that of the normal scanning, the period of the vertical synchronization signal is ¹⁄₁₆ that of the normal scanning. By setting the number of scan lines and the scan width smaller than those of the normal scanning as described above, the periods of the vertical and horizontal synchronization signals can be made shorter, reducing the time required to retrieve one frame.

Figure 9A:
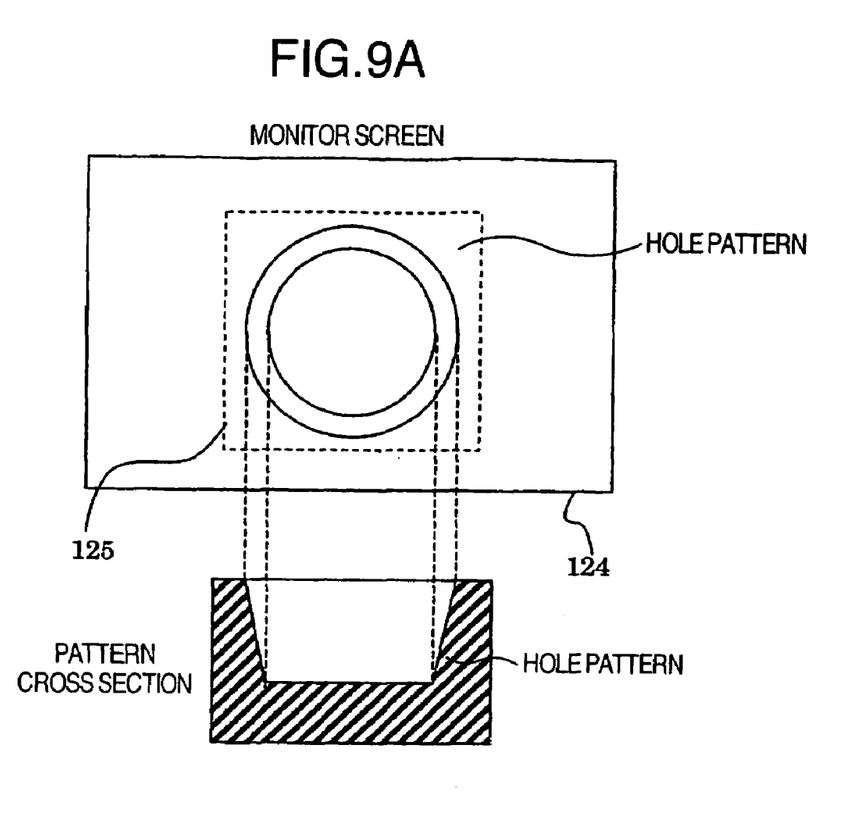
FIGS. 9A and 9B show an example case of measuring a hole pattern.
Figure 9B:
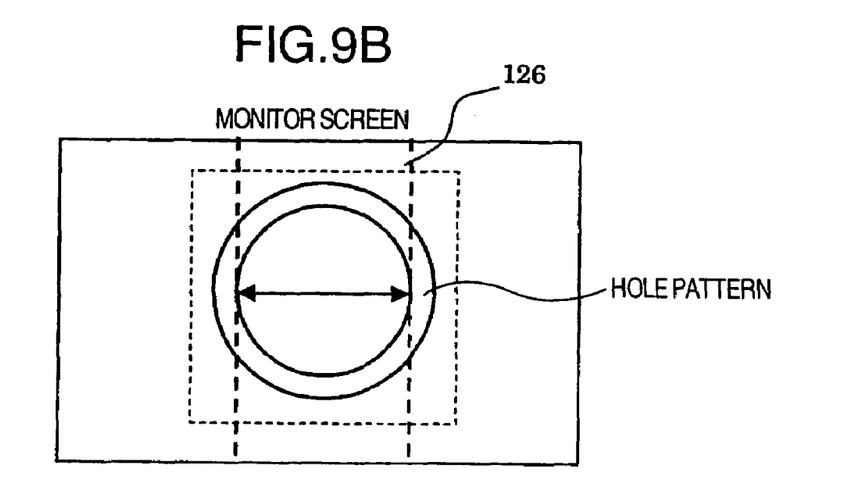

An example application of this scanning is a dimension measurement. This is explained in an example case of measuring a bottom diameter of a hole pattern shown in FIG. 9. It is assumed that the normal interlaced scanning is chosen as the order of scanning, the normal 512 lines as the number of scan lines, ¹⁄₁ as the scan width, and 1 as the total frame number and that an image of a target to be measured is produced in one scanning operation at a desired magnification and displayed on the monitor screen. An image of the normally scanned area, though its image resolution is low because the total frame number is 1, is displayed on the monitor screen as shown in FIG. 9A, so the user can recognize the hole pattern being measured. An area 125 whose scan line number and scan width are reduced by the parameters chosen in the selection page of FIG. 3 is displayed on the screen over the rough image to specify an area the user wishes to measure more precisely. Then, the scanning is performed for a desired number of frames specified in the selection page; image signals for the scanned frames are summed up; and an image with an improved S/N is displayed on the monitor screen. Then, vertical cursor lines 126 are aligned to a portion to be measured, as shown in FIG. 9B, for dimension measurement.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A specimen dimension measurement method comprising steps of scanning electron beam to a scanning region on the specimen, accumulating signals obtained by a plurality of scan to said scanning region, and measuring dimension of a pattern formed in said scanning region in accordance with said accumulated signal, wherein
    carrying out said plurality of scanning at one scanning position of said scanning region;
    then carrying out said plurality of scanning at another different scanning position other than said scanning position;
    carrying out scanning to said scanning region by repeating said plurality of scanning to said another different scanning position, and
    measuring dimension of said pattern in accordance with accumulated result obtained by said plurality of scanning to said scanning region.

2. A method according to claim 1, wherein while carrying outs aid plurality of scanning in said each of scanning position, a time interval for scanning said plurality of scanning is set short compared to time interval of scanning at said each of scanning position when carrying out interlace scanning to said scanning region.

3. An electron microscope according to claim 1, wherein said scanning deflector, while carrying a plurality of scanning at said each scanning position, a time interval for scanning among said plurality of each scanning position is set shorter compare to scanning time period at said each scanning position for carrying out interlace scanning at said scanning region.

4. A scanning electron microscope comprising, an electron beam source, a scanning deflector for scanning the electron beam emitted from said electron beam source, and measuring pattern dimension of a pattern formed on said specimen in accordance with accumulated result of signal emitted from said specimen by a plurality of scanning of said electron beam, wherein;
    said scanning deflector carries out said plurality of scanning to a single scanning position of said scanning region on the specimen; then carrying out said plurality of scanning to another different scanning position other than said scanning position and carrying out scanning to said scanning region by repeating the plurality of scanning to said different scanning position.

5. An image displaying method comprising steps of scanning electron beams for each plurality of frames to a specimen, and displaying image of said scanning region at an predetermined region on said display apparatus in accordance with said scanning, wherein;
    scanning said electron beam by narrowing scanning region in a perpendicular direction to said electron bean scanning line compared to displaying image in a predetermined region on said display apparatus, and measuring pattern dimension of which dimension is decreased by scanning of said electron beam in accordance with said scanning of said electron beam.

* * * * *